United States Patent [19]

Wang

[11] Patent Number: 5,059,674

[45] Date of Patent: Oct. 22, 1991

[54] CURED ARYLCYCLOBUTENE ETHER SPIRODILACTAM

[75] Inventor: Pen C. Wang, Houston, Tex.

[73] Assignee: Shell Oil Company, Houston, Tex.

[21] Appl. No.: 506,037

[22] Filed: Apr. 9, 1990

Related U.S. Application Data

[62] Division of Ser. No. 324,872, Mar. 17, 1989, Pat. No. 4,968,810.

[51] Int. Cl.$^5$ .............................................. C08G 83/00
[52] U.S. Cl. .................................. 528/210; 528/323; 528/330
[58] Field of Search .................... 528/210, 323, 330

[56] References Cited

U.S. PATENT DOCUMENTS

| | | | |
|---|---|---|---|
| 4,540,763 | 9/1985 | Kirchhoff | 526/281 |
| 4,675,370 | 6/1987 | Tan et al. | 526/259 |
| 4,687,815 | 8/1987 | Wong | 525/271 |
| 4,847,388 | 7/1989 | Wang | 548/410 |
| 4,888,408 | 12/1989 | Wang | 528/96 |
| 4,968,810 | 11/1990 | Wang | 548/410 |

OTHER PUBLICATIONS

Cram et al., "Organic Chemistry," 2nd Ed., 243 (?) (date not provided by USPTC in parent).
Cava et al., *J. Am. Chem. Soc.*, 79, pp. 1706–1709 (1956).

*Primary Examiner*—Harold D. Anderson

[57] ABSTRACT

Arylcyclobutenealkyl ethers of hydroxyaryl-substituted 1,6-diaza [4.4] spirodilactams having a hydroxyaryl substituent on each spiro ring nitrogen atom are self-curing upon application of heat to produce cured products of relatively high glass transition temperature having good physical properties.

11 Claims, No Drawings

CURED ARYLCYCLOBUTENE ETHER SPIRODILACTAM

This is a division of application Ser. No. 324,872, filed Mar. 17, 1989, now U.S. Pat. No. 4,968,810.

FIELD OF THE INVENTION

This invention relates to a novel class of ether derivatives of a hydroxyaryl-substituted spirodilactam. More particularly, the invention relates to arylcyclobutenealkyl ethers of a hydroxyaryl-substituted 1,6-diaza [4.4]spirodilactam wherein the hydroxyaryl-containing substituents are located on the spiro ring nitrogen atoms, and to cured products obtained by heating the arylcyclobutenemethyl ethers.

BACKGROUND OF THE INVENTION

The curing of monomeric materials to produce thermoset resins is well known in the art. In general, the curable monomers have at least one and customarily more than one active group which serves as the reactive site for a curing or crosslinking reaction to produce the cured thermoset resins which are typically highly crosslinked. The curing or crosslinking of many thermoset resins, for example, the curing of epoxy resins, requires the use of a curing agent, catalytic or stoichiometric, to cause the crosslinking reaction to proceed at an acceptable rate. Certain other monomers cure in the absence of added curing agent, but only upon application of high intensity energy, e.g., UV light. Even in the presence of most curing agents the rate of crosslinking is unduly slow and the addition of an accelerator is generally required to obtain sufficiently rapid curing.

There are some monomers in which the active sites are such that no added curing agent is required and such monomers cure upon application of heat at an acceptable rate. These monomers are termed "self-curing". One class of the self-curing monomers includes within the molecular structure one or more moieties of an arylcyclobutene, preferably a benzocyclobutene. These monomers are cured by reaction with a conventional curing agent but are also self-curing. Without wishing to be bound by any particular theory, it appears probable that upon application of heat the cyclobutene ring undergoes ring opening to produce active intermediates which crosslink by undergoing rapid reaction with adjacent molecules. The resulting cured thermoset resins have properties of rigidity and strength.

A series of U.S. patents to Kirchhoff, of which U.S. Pat. No. 4,540,763 is illustrative, describes the production and curing of a large number of benzocyclobutene derivatives, including ethers of bis(hydroxyphenyl)alkanes, wherein the ether linking group which links the phenyl of the bis(hydroxyphenyl)alkane to the benzocyclobutene moiety is attached directly to the six-membered ring of the benzocyclobutene. A U.S. patent to Tan et al, U.S. Pat. No. 4,675,370, discloses benzocyclobutene derivatives in which the six-membered ring of the benzocyclobutene is attached to a substituent having an acetylenic group by an aromatic link. A related series of Wong, of which U.S. Pat. No. 4,687,815 is illustrative, discloses alkenyl substituted benzocyclobutenes. A Research Disclosure, source unknown, discloses benzocyclobutenes in which the six-membered ring of the benzocyclobutene is attached to a polyvalent organic or inorganic group which is preferably hydrocarbon or contains silicon, nitrogen or oxygen heterocyclic moieties. A somewhat different type of benzocyclobutene ether derivative is disclosed and claimed by copending U.S. patent application Ser. No. 349,546, filed, May 9, 1989 U.S. Pat. No. 4,943,665 directed to benzocyclobutenealkyl ethers of bis(hydroxyphenyl)alkanes. These ethers have an alkylene linking group attached to the six-membered ring of the benzocyclobutene ring system and through an ether oxygen is attached to the phenyl group of the bis(hydroxyphenyl)alkane. Other ethers having a hydroxyaryl-substituted 1,6-diaza [4.4] spirodilactam group present are disclosed and claimed in copending U.S. patent application Ser. No. 245,433, filed Sept. 16, 1988 now U.S. Pat. No. 4,897,388. Alkenyl and alkenyl esters, e.g., allyl or propargyl ethers of 1,6-di(4-hydroxyphenyl)-1,6-diazaspiro4.4]nonane-2,7-dione, are illustrative and are disclosed as being self-curing.

It would be of advantage, however, to provide additional benzocyclobutene-type ether derivatives wherein other polycyclic structures are present.

SUMMARY OF THE INVENTION

This invention provides a novel class of arylcyclobutenealkyl ethers having additional polycyclic structures present within the molecule. More particularly, the invention relates to arylcyclobutenealkyl ethers of a hydroxyaryl-substituted 1,6-diaza [4.4]spirodilactam in which the hydroxyaryl substituents are located the spiro ring nitrogen atoms. The resulting monomeric ethers crosslink without the presence of added curing agent to produce a crosslinked, insoluble, cured product having good properties. The invention further relates to the methods of producing the novel ethers and to the cured products obtained by heating the ethers.

DESCRIPTION OF THE INVENTION

The arylcyclobutenealkyl portion of the novel ethers of the invention is provided by an arylcyclobutene moiety having an alkylene linking group attached to a six-membered aromatic ring of the arylcyclobutene moiety and to an electron-withdrawing group. This arylcyclobutene compound reacts with a salt, preferably an alkali metal salt, of the hydroxyaryl-substituted 1,6-diaza 4.4] spirodilactam to produce the ethers of the invention.

The arylcyclobutene compound reactant is a compound of the formula

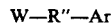

W—R''—Ar     (I)

wherein W is an electron-withdrawing group, R'' is an alkylene group of up to 10 carbon atoms inclusive and Ar represents an arylcyclobutene ring system of up to 4 aromatic rings and up to 30 carbon atoms inclusive which contains at least one cyclobutene ring fused to an aromatic ring. Suitable aromatic ring systems are illustrated by the single aromatic ring compound benzene, the fused ring system compounds naphthalene, anthracene and phenanthrene, the directly-joined aromatic ring system compounds biphenyl and 1-phenylnaphthalene or the alkylene-joined aromatic ring system compounds of two or more aromatic rings joined by an alkylene group, e.g., diphenylalkanes such as diphenylmethane and 2,2-diphenylpropane. The preferred aromatic ring system is a single aromatic ring and the preferred arylcyclobutene moiety is benzocyclobutene. The arylcyclobutene moiety is otherwise unsubstituted except for the W—R"— group located on a carbon atom of a six-membered ring or is substituted in other ring positions with groups such as cyano or lower alkyl, i.e., alkyl of up to 4 carbon atoms inclusive such as methyl or ethyl, which groups are inert under the conditions at which production of the ethers of the invention takes place. The preferred arylcyclobutene moieties are unsubstituted except for the W—R"— substituent.

The term W in the above formula 1 is an electron-withdrawing group, by which is meant a substituent group which more easily than hydrogen withdraws or attracts electrons from other locations within the molecule or alternatively expressed is considered a readily "leaving" or "departing" group in electrophillic substitution reactions. Illustrative of such groups are cyano, halo, hydrocarbyloxy, alkanoyl, alkylsulfonyl and alkylsulfonoyl. The preferred electron withdrawing group W is halo, e.g., fluoro, chloro, bromo or iodo, particularly the middle halogens chloro or bromo. The R" alkylene group is a straight-chain, branched-chain or cyclic alkylene group and is illustrated by methylene, 1,3-propylene, 2-methyl-1,3-propylene and 1,4-cyclohexylene. The preferred R" group is methylene and the preferred arylcyclobutene alkyl reactants are halomethylbenzocyclobutenes, particularly chloromethylbenzocyclobutene and bromoethylbenzocyclobutene.

These W-alkylarylcyclobutenes are known compounds or are produced by known methods. For example, chloroalkylbenzocyclobutenes are produced by the method of Ewing et al, J. Chem. Soc. Chem. Comm., 207 (1979). The compound 4-chloromethylbenzocyclobutene is produced by alkylation of p-methylbenzyl chloride with formaldehyde in the presence of zinc chloride and hydrogen chloride. The resulting 2,4-di(-chloromethyl)toluene is heated at 700° C. in vacuo to give the desired product. Similar reaction of o-methylbenzyl chloride results in production of a 1:2 mixture of 3-chloromethylbenzocyclobutene and 4-chloromethylbenzocyclobutene which is separated by conventional methods or alternatively is employed without separation to produce an isometric mixture of ethers.

The hydroxyaryl 1,6-diaza 4.4] spirodilactam moieties of the ethers of the invention are derived from a 1,6-diazaspiro[4.4]nonane -2,7-dione which is substituted on each spiro ring nitrogen atom with a hydroxyaryl-containing substituent and is optionally substituted in other spiro ring positions with acyclic or fused acyclic substituents. One class of such spirodilactams comprises spirodilactams of up to 60 carbon atoms inclusive which are represented by the formula

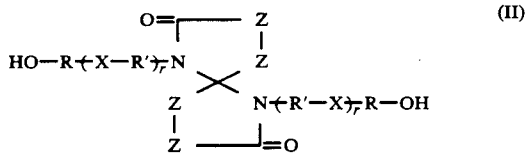

(II)

wherein R independently is aromatic of up to 15 carbon atoms and up to 2 aromatic rings, inclusive, R' independently is R or aliphatic of up to 10 carbon atoms inclusive, r independently is 0 or 1, X independently is a direct valence bond, alkylene of up to 8 carbon atoms inclusive, oxy, thio, sulfonyl, carbonyl, dioxyphenylene, 2,2-di(oxyphenyl)propane, di(oxyphenyl) sulfone or dioxydiphenylene, and Z independently is

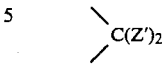

in which Z' independently is hydrogen, lower alkyl, preferably methyl, halo, preferably the lower halogens fluoro and chloro, or aryl, preferably phenyl, or Z is such that two adjacent Z moieties taken together form a ring system Z" of from 5 to 7 ring atoms, up to two of which are heteroatoms selected from nitrogen, oxygen or sulfur with the remainder of the ring atoms being carbon atoms, there being up to 15 carbon atoms in each Z", two of which connect the carbon atoms connected by the adjacent Z moieties. R and R' independently are hydrocarbyl containing only atoms of carbon and hydrogen or are substituted hydrocarbyl additionally containing other atoms such as halogen, preferably middle halogen, as inert monovalent carbon atom substituents.

Spirodilactams of a considerable variety of structures are therefore suitably employed as precursors of the ethers of the invention. In the embodiment wherein the Z moieties of the above formula II are not a portion of a fused ring substituent and are therefore acyclic, i.e., each Z is

the spirodilactams are illustrated by 1,6-di(4-hydroxyphenyl)-1,6-diazaspiro [4,4]nonane-2,7-dione, 1,6-di(3-hydroxy-4-chlorophenyl)-3,8-dimethyl -1,6-diazaspiro[4,4]nonane-2,7-dione, 1,6-di[4-(3-hydroxybenzoyl)phenyl]-1,6-diazaspiro[4.4]nonane-2,7-dione, 1,6-di(4-hydroxyphenyl)-3,3,4,4,8,8,9,9-octamethyl-1,6-diazaspiro[4.4]nonane-2,7-dione, 1,6-di[4-(4'-hydroxybiphenyl)]-3,3,-dimethyl-1,6-diazaspiro[4.4]nonane-2,7-dione, 1,6-di[2-(4-hydroxyphenyl)propyl]-1,6-diazaspiro[4.4]nonane-2,7-dione, 1,6-di[4-(4-hydroxyphenylisopropyl)phenyl-1,6-diazaspiro[4.4]nonane-2,7-dione and 1,6-di(4-hydroxyphen),1)-3,4,8,9-tetrafluoro-1,6-diazaspiro[4.4]nonane-2,7-dione. In the embodiment where adjacent Z moieties on each spiro ring form fused ring substituent, illustrative spirodilactams include 1,6-di(4-hydroxyphenyl)-3,4,8,9-dibenzo-1,6-diazaspiro[4.4]nonane-2,7-dione, 1,6-di[4-(4-hydroxylphenyloxy)phenyl]-3,4,8,9-di(pyrido)-1,6-diazaspiro[4.4]nonane-2,7-dione and 1,6-di[4-(4-hydroxyphenylthio)phenyl]-3,4,8,9-di(cyclopentano)-1,6-diazaspiro[4.4]-nonane-2,7-dione. Also suitable are those spirodilactams wherein one spiro ring has a fused cyclic substituent and the other spiro ring is free of fused cyclic substituents, e.g., 1,6-di(4-hydroxyphenyl)-3,4-benzo-8-methyl-1,6-diazaspiro[4.4]nonane-2,7-dione and 1,6-di[1-(4-hydroxynaphthyl)]3,4-cyclohexano-1,6-diazaspiro4.4]nonane-2,7-dione.

In general, the hydroxyaryl-substituted spirodilactams of the above formula II wherein R and R' are aromatic and hydrocarbon are preferred, especially such compounds wherein each r is 0. The class of 1,6-di(hydroxyphenyl) spirodilactams is particularly preferred. Within the spirodilactam portion of the molecule, compounds wherein both spiro rings are free of fused cyclic substituents or compounds wherein both spiro rings have a fused cyclic substituent are preferred. The compound 1,6-di(4-hydroxyphenyl) -1,6-diazaspiro[4.4]nonane-2,7-dione is an especially preferred member of the former class and 1,6-di(4-hydroxyphenyl)-3,4,8,9-dibenzo-1,6-diazaspiro[4.4]nonane-2,7-dione is an especially preferred member of the latter class.

The hydroxyaryl-substituted spirodilactams are compounds which are described in more detail and are claimed as compositions of matter in copending U.S. patent application Ser. No. 245,618, filed Sept. 16, 1988 U.S. Pat. No. 4,939,251. The general method of production, also described and claimed in this copending patent application and copending U.S. application Ser. No. 172,000 filed Mar. 23, 1988 and Ser. No. 172,052, filed Mar. 23, 1988, each of which is incorporated herein by reference, is by reaction of a hydroxy-containing primary amino compound and a spirodilactam precursor. In terms of the spirodilactam of formula II, the hydroxy-containing primary amino compound is represented by the formula

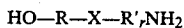  (III)

wherein R, R', r and X have the previously stated meanings. The spirodilactam precursor is a 4-oxoheptanedioic acid compound or a 1,6-dioxaspiro[4.4]nonane-2,7-dione, a spirodilactone. In terms of the spirodilactam of formula II, the 4-oxoheptanedioic acid compound spirodilactam precursors are represented by the formula

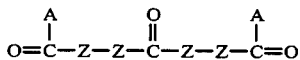  (IVa)

wherein Z has the previously stated meaning and A independently is hydroxy, lower alkoxy of up to 4 carbon atoms inclusive or halo, preferably middle halo. The spirodilactone spirodilactam precursor, in terms of the spirodilactam of formula II is represented by the formula

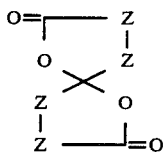  (IVb)

wherein Z has the previously stated meaning.

The acyclic 4-oxoheptanedioic acid compounds employed as spirodilactam precursors are known compounds or are produced by known methods, but certain of the esters, i.e., acyclic compounds of formula IVa wherein A is alkoxy, are conveniently produced by the process disclosed and claimed in copending U.S. Pat. application Ser. No. 171,999, filed Mar. 23, 1988 now U.S. Pat. No. 4,800,231. This process involves the reaction of formaldehyde and an unsaturated carboxylic acid ester such as methyl acrylate, propyl methacrylate or ethyl crotonate in the presence of a catalyst system which comprises a thiazolium salt and a tertiary amine. Interconversion of the esters, acids and acid halides of formula IVa is by conventional methods. The production of 4-oxoheptanedioic acid compounds of formula IVa having cyclic substituents is by the general process of Cava et al, J. Am. Chem. Soc., 77, 6022 (1955). The spirodilactones of formula IVb are produced according to the general teachings of Pariza et al, Synthetic Communications, Vol. 13 (3), pp. 243-254 (1983) or by the general process of Conover et al, U.S. Pat. No. 1,999,181.

The hydroxy-containing primary amino compound and the spirodilactam precursor react in a molar ratio of 2:1 although in practice reactant ratios of from about 8:1 to about 1:1.5 are satisfactory. Reactant ratios of hydroxy-containing primary amino compound to spirodilactam precursor which are substantially stoichiometric are preferred. Reaction is conducted in a liquid phase solution in an inert reaction diluent such as an N-alkylamide, e.g., N,N-dimethylformamide, N,N-dimethylacetamide or N-methyl-2-pyrrolidone. Reaction takes place at an elevated temperature, typically from about 80° C. to about 200° C., and at a pressure sufficient to maintain the reaction mixture in a liquid phase. Such pressures are customarily up to about 20 atmospheres. Subsequent to reaction the spirodilactam product is recovered from the product mixture by conventional methods such as solvent removal, precipitation or chromatographic separation. Recovery of the spirodilactam is not required, however, and particularly in the cases where substantially stoichiometric quantities of reactants were employed the spirodilactam may be further reacted in situ, without isolation.

The W-alkylarylcyclobutene compound is reacted with a salt of the hydroxyaryl-substituted spirodilactam to produce the novel ethers of the invention. Although a variety of hydroxyaryl-substituted spirodilactam salts are satisfactory, the preferred salts are alkali metal salts and lithium, sodium, potassium, rubidium or cesium salts are satisfactory. Particularly preferred are the sodium and potassium salts. The alkali metal salts are typically prepared by contacting a solution of the hydroxyaryl-substituted spirodilactam, in a suitable reaction diluent, with a slight stoichiometric excess of a strong alkali metal base, e.g., the hydroxide, carbonate or bicarbonate. The reaction diluent is a polar, inert diluent and is the same as that in which the spirodilactam was produced, i.e., an N-alkylamide, or a different diluent such as a glycol, ether, ketone, sulioxide or sulfone. In a preferred embodiment, the diluent employed for production of the salt is one with which water forms a low-boiling azeotrope or in the alternative a minor quantity of a second reaction diluent is employed, e.g., a alkylated benzene such as toluene or ethylbenzene, with which water azetropes. Either modification allows the water which is present or formed in the neutralization reaction to be removed conveniently through azeotropic distillation. Other conventional methods for water removal may alternatively be employed such as extraction. The alkali metal salt of the spirodilactam reactant is isolated, if desired, by conventional techniques such as solvent removal or precipitation. Isolation of the salt is not necessary however, and the alkali metal salt may be further reacted in situ to produce the ethers of the invention.

The reaction of the salt of the hydroxyaryl-substituted spirodilacta and the W-alkylarylcyclobutene is accomplished by contacting the two reactants under reaction conditions. In one embodiment, the arylcyclobutene reactant is present during the formation of the salt of the hydroxyaryl-substituted spirodilactam and, subsequent to the removal of water produced during the preparation of the salt, reaction of the salt with the arylcyclobutene reactant is initiated as by raising the temperature of the reaction mixture. In another embodiment, the arylcyclobutene reactant( is added to a solution of the salt of the hydroxyaryl-substituted spirodilactam in the media of its production or which has been isolated and re-dissolved in the same or a different reaction diluent.

By whatever procedure, the arylcyclobutene reactant and the salt of the hydroxyaryl-substituted spirodilactam are contacted in a molar ratio of from about 8:1 to about 1:4, although a ratio of the reactants that is substantially stoichiometric, i.e., substantially 2:1, is preferred. The etherification reaction is conducted at an elevated temperature in a liquid phase solution. Reaction temperatures are typically from about 25° C. to about 250° C. but preferably are from about 50° C. to about 200° C. Suitable reaction pressures are those which are sufficient to maintain the reaction mixture in a liquid phase. Such pressures are up to about 20 atmospheres but more often are from about 0.8 atmospheres to about 10 atmospheres. Subsequent to reaction, the ether product is recovered through the use of well-known techniques such as precipitation, extraction or solvent removal.

The novel monomeric ethers of the invention are ethers wherein each hydroxyaryl substituent of the spirodilactam has been etherified through loss of the acidic hydrogen and condensation with the arylcyclobutenealkyl moiety illustratively obtained by loss of the electron-withdrawing group from the W-alkylarylcyclobutene reactant. In terms of the reactants as described above, formulas I and 11, the ether products are represented by the formula

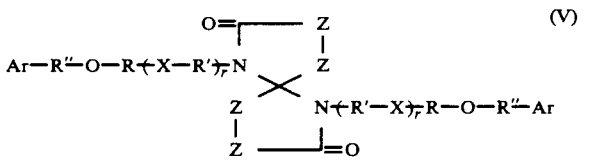

wherein Ar, R, R', R'', r, X and Z have the previously stated meanings. The nomenclature of such ether products is not always easily determined because of the complexity thereof but an illustrative product is 1,6-di[4-(4-benzocyclobutenemethyloxy)phenyl]-1,6-diazaspiro[4.4]nonane-2,7-dione illustratively produced by the reaction of 4-chloromethylbenzocyclobutene and the sodium salt of 1,6-di(4-hydroxyphenyl)-1,6-diazaspiro[4 4]nonane-2,7-dione. The identity of other products will be apparent from consideration of the formulas for the reactants and the diether product.

The novel ether products of the invention are relatively low-melting solids with melting points frequently within the 50° C. to 150° C. range. The ethers are self-curing and will cure or crosslink without the presence of added curing agent or accelerator by heating the ether to a temperature above 150° C., preferably to a temperature from about 175° C. to about 275° C. The cured products are rigid polymers with a highly crosslinked structure and good physical strength and resistance to common solvents. The ethers are processed by methods which are conventional for curing monomeric compounds by application of heat. The cured products have relatively high glass transition temperatures and are useful in adhesive formulations and as structural and coating materials for use in aerospace and electronic applications. Thermosetting resin compositions comprising the ethers of the invention in combination with at least one additional polymerizable monomer are described and claimed in copending U.S. Pat. application Ser. No. 324,866 , filed Mar. 17, 1989 U.S. Pat. No. 4,921,931.

The invention is further illustrated by the following Illustrative Embodiments which should not be construed as limiting the invention.

ILLUSTRATIVE EMBODIMENT I

To a 2 liter three-necked round-bottomed flask was charged 16.92 g (0.05 mole) of 1,6-di(4-hydroxyphenyl)-1,6-diazaspiro[4.4]nonane-2,7-dione, 7.6 g (0.055 mole) of potassium carbonate, 50 ml of toluene and 200 ml of N,N-dimethylacetamide. The flask and contents were heated to 150°-160° C. and the water present or formed was removed by azeotropic distillation. When water removal was complete, the temperature was lowered to 80°-90° C. and 16.77 g (0.11 mole) of chloromethylbenzocyclobutene in 50 ml of N,N-dimethylacetamide was added over thirty minutes. The reaction temperature was raised to 150° C. and maintained at that temperature for 12 hours. The resulting mixture was cooled and filtered. The filtrate was concentrated to about 75 ml and slowly poured into 3 liters of water. The precipitated product was recovered by filtration, washed with water and dried in a vacuum oven at 80° C. The dried product had a melting point of 127° C. and the nuclear magnetic resonance spectra of the product were consistent with the structure 1,6-di[4-(4-benzocyclobutenemethyloxy)phenyl]-1,6-diazaspiro[4.4]nonane-2,7-dione.

ILLUSTRATIVE EMBODIMENT II

The ether product of illustrative Embodiment I was cured by heating at 200° C. for 2 hours and at 220° C. for an additional 4 hours. The resulting cured product had a glass transition temperature of 267° C.

What is claimed is:

1. The cured product obtained by heating to a temperature above 150° C. the ether of the formula

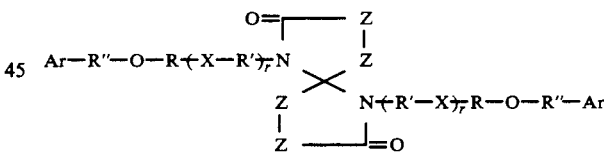

wherein Ar is an arylcyclobutene ring system having up to 4 aromatic rings and up to 30 carbon atoms, inclusive, R'' is alkylene of up to 10 carbon atoms inclusive attached to a six-membered ring of Ar, R is aromatic of up to 15 carbon atoms and up to two aromatic rings, inclusive, R' is R, X is a direct valence bond, or X is alkylene of up to 8 carbon atoms, inclusive, oxy, thio, sulfonyl, carbonyl, dioxydiphenylene, 2,2-di(oxyphenyl)propane di(oxyphenyl)sulfone or dioxydiphenylene, r is 0 or 1 and Z independently is

in which Z' independently is hydrogen, lower alkyl, lower halo or phenyl, or Z is such that adjacent Z groups taken together form a ring system Z'' of from 5 to 7 ring atoms, up to two of which are heteroatoms selected from nitrogen, oxygen, or sulfur with the remainder of the ring atoms being carbon atoms, there being up to 15 carbon atoms in each Z", two of which form a bridge between the carbon atoms connected by the adjacent Z groups.

2. The cured product according to claim 1 wherein in the ether Ar—R"— is benzocyclobutenemethyl.

3. The cured product according to claim 2 wherein in the ether each r is 0.

4. The cured product according to claim 3 wherein in the ether each R is phenylene.

5. The cured product according to claim 4 wherein in the ether Z is

6. The cured product according to claim 5 wherein in the ether Z' is hydrogen or methyl.

7. The cured product according to claim 6 wherein in the ether each Z' is hydrogen.

8. The cured product according to claim 7 wherein in the ether R is p-phenylene.

9. The cured product according to claim 4 wherein in the ether adjacent Z groups are Z".

10. The cured product according to claim 9 wherein in the ether Z" is benzo.

11. The cured product according to claim 10 wherein in the ether R is p-phenylene.

* * * * *